United States Patent [19]

Winn et al.

[11] 4,145,422
[45] Mar. 20, 1979

[54] AMINOMETHYLENE OXINDOLES

[75] Inventors: Martin Winn, Deerfield; John J. Kyncl, Lake Forest, both of Ill.

[73] Assignee: Abbott Laboratories, North Chicago, Ill.

[21] Appl. No.: 830,722

[22] Filed: Sep. 6, 1977

[51] Int. Cl.² ............... A61K 31/495; C07D 401/00; C07D 403/00
[52] U.S. Cl. .................................. 424/250; 542/444
[58] Field of Search ...................... 424/250; 542/444

[56] References Cited

U.S. PATENT DOCUMENTS

| 3,466,287 | 9/1969 | Archer | 424/250 |
| 3,562,278 | 2/1971 | Archer | 424/250 |

OTHER PUBLICATIONS

Chemical Abstracts, vol. 67:3031e, vol. 71:112732n.

Primary Examiner—Donald B. Moyer
Attorney, Agent, or Firm—Robert L. Niblack; Gildo E. Fato

[57] ABSTRACT

This invention provides aminomethylene oxindole compounds represented by the formula

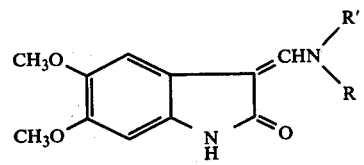

wherein R is H or loweralkyl; R' is loweralkyl, aralkyl, or R and R' taken together form a chain of the formula

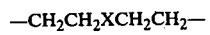

wherein X is $CH_2$ or NR'' where R'' is loweralkyl, loweralkanoyl, aroyl, alkoxycarbonyl or aryl; and the pharmaceutically acceptable acid addition salts thereof.

The compounds of this invention are useful as antihypertensive agents.

10 Claims, No Drawings

AMINOMETHYLENE OXINDOLES

BACKGROUND OF THE INVENTION

Hypertension describes a symptom of several disease entities, both of known and unknown etiology, the elevated blood pressure being the measurement indicating its presence. A persistently elevated blood pressure is considered a serious symptom. High blood pressure can be temporary or can result from known causes such as kidney or artery disease. While some types of hypertension respond only to surgery and in others sedatives may comprise the sole therapy, most forms of hypertension are treated by means of chemotherapy. Chemical entities capable of lowering blood pressure in mammals such as the antihypertensive agents provided by the present invention, are consequently highly desirable.

Untreated hypertension produces risk of cardiovascular complications such as strokes, myocardial infarction and the like which lower the quality of life and life expectancy, whereas drug therapy can significantly improve the longevity of the hypertensive population.

Detailed Description of the Invention

The invention relates to aminomethylene oxindoles which are useful as antihypertensive agents. the oxindoles are compounds represented by the formula:

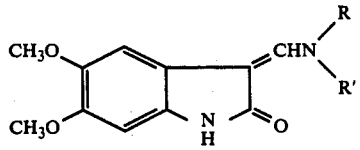

wherein R is H or loweralkyl, R' is loweralkyl or aralkyl, or R and R' taken together form a chain of the formula
—$CH_2CH_2X$ $CH_2CH_2$—
wherein X is $CH_2$ or NR" where R" is loweralkyl, loweralkanoyl, aroyl, alkoxycarbonyl or aryl; and the pharmaceutically acceptable acid addition salts thereof.

The term "loweralkyl", as used herein, refers to $C_1$ to $C_6$ alkyl groups including methyl, ethyl, n-propyl isopropyl, n-butyl, tertiary butyl, n-pentyl, iso-pentyl, n-hexyl and the like.

The term "aralkyl" refers to a straight or branched alkyl group of 1 to 10 carbon atoms where one of the hydrogen atoms of the alkyl group is substituted by phenyl or a substituted phenyl.

As used herein, the term "loweralkanoyl" means saturated, monovalent, aliphatic radicals, derived from a monocarboxylic acid including straight or branched chain radicals of 2 to 6 carbon atoms, as illustrated by, but not limited to acetyl, propionyl, α-methylpropionyl, butyryl, hexanoyl, and the like.

The term "alkoxy" refers to alkoxy groups having a total of no more than six carbon atoms such as methoxy, ethoxy, n-propoxy, iso-propoxy and the like.

The present oxindoles may generally be prepared as illustrated below in Scheme A where R and R' are as defined above:

Scheme (A):

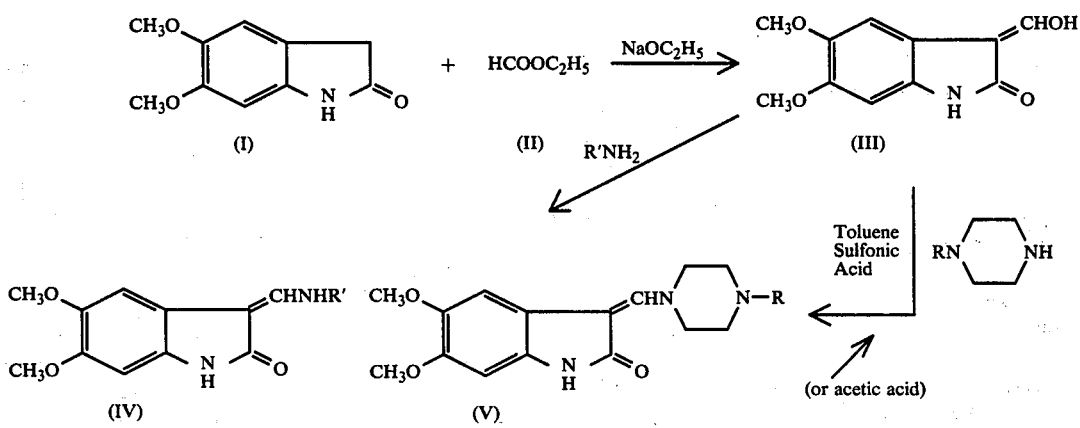

As illustrated above in Scheme (A), the intermediate, 5,6-dimethoxy oxindole (I) is reacted with ethyl ortho formate (II) to provide 5,6-dimethoxy-3-hydroxymethylene oxindole (III). This oxindole (III) is then reacted with primary or secondary amines in refluxing benzene in the presence of acetic acid or toluene sulfonic acid to yield 5,6-dimethoxy-3-(substituted amino methylene) oxindoles (IV) or (V), respectively.

The compounds which may be prepared according to the general process scheme, illustrated and described above, include:

(VI)  5,6-Dimethoxy-3-(2-methylpropyl-aminomethylene)oxindole

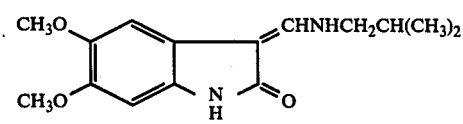

(VII)  5,6-Dimethoxy-3(4-carbethoxy piperazino) methylene oxindole

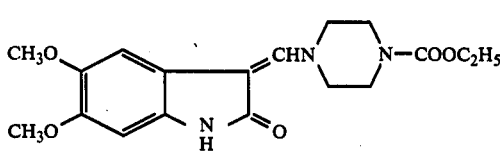

(VIII)  5,6-Dimethoxy-3(4-furoyl piperazino)methylene oxindole

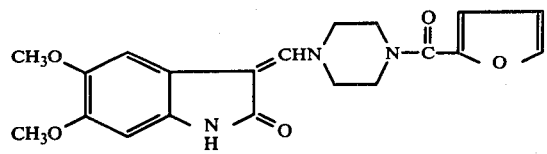

(IX) 5,6-Dimethoxy-3[4(2-methylpropyloxy carbonyl)piperazino]methylene oxindole

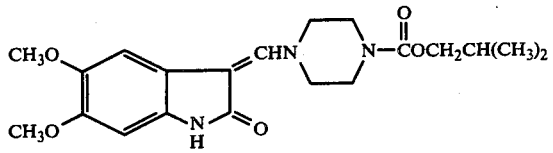

(X) 5,6-Dimethoxy-3[4(3,4-dimethoxyphenyl) piperazino]methylene oxindole

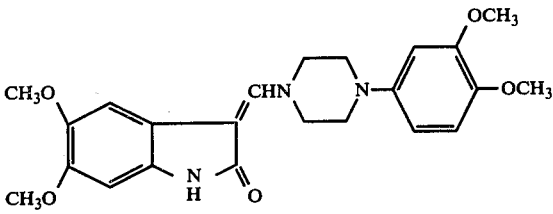

(XI) 5,6-Dimethoxy-3[4(tetrahydropyran-2-carbonyl)piperazinyl]methylene oxindole

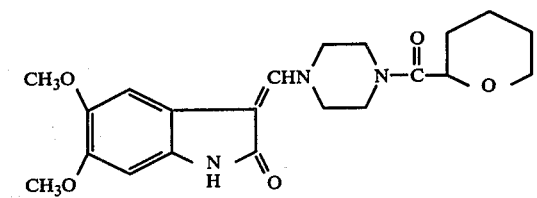

(XII) 5,6-Dimethoxy-3[2(3,4-dimethoxyphenyl) ethylaminomethylene]oxindole

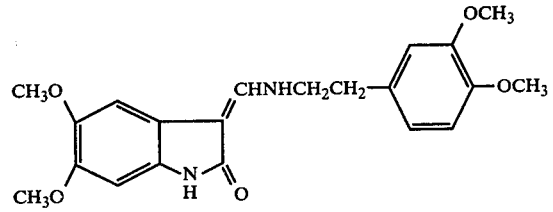

(XIII) 5,6-Dimethoxy-3(1-piperidinomethylene) oxindole

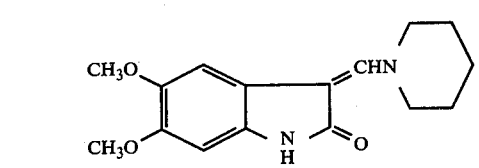

(XIV) 5,6-Dimethoxy-3(4-Methyl-1-piperazino methylene) oxindole

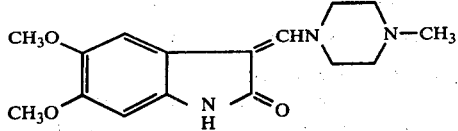

(XV) 5,6-Dimethoxy-3(3,4-dimethoxybenzyl) aminomethylene oxindole

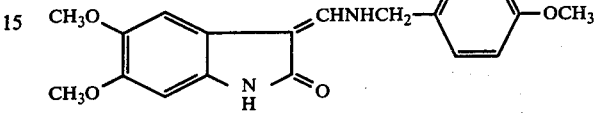

(XVI) 5,6-Dimethoxy-3[2-(2-pyridylethyl) methylamino oxindole

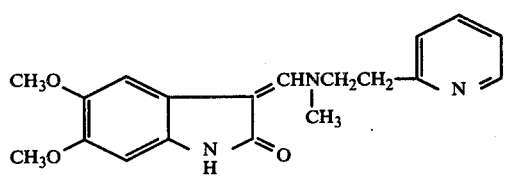

The compounds of this invention are useful as antihypertensive agents. The compounds are effective at dosages generally of from 0.1 to 500 mg./kg. of body weight. To illustrate their administration, the present compounds are formulated with a pharmaceutically acceptable carrier into compositions.

The following examples are presented to further illustrate the present invention.

EXAMPLE 1

5,6-Dimethoxy-3-hydroxymethylene oxindole (III)

To a warm solution of 1.5 g. sodium in 35 ml. ethanol was added 10 g. of 5,6-dimethoxy oxindole [J. Am. Chem. Soc. 77 3844 (1955)]. Then 30 ml. ethyl formate was added. A solid formed. The mixture was stirred and heated 10 minutes. A stream of nitrogen was blown over the mixture to evaporate as much solvent as possible. Then a solution of 6.5 ml. concentrated hydrochloric acid and 50 ml. water was added. The resulting clear solution was concentrated in vacuum and the resulting solid filtered and washed with ice water. Yield: 10.55 g., m.p. 216°-217° C.

EXAMPLE 2

5,6-Dimethoxy-3(2-methylpropyl-aminomethylene oxindole (VI)

5,6-Dimethoxy-3-hydroxymethylene oxindole (6.40 g.) was suspended in 60 ml. benzene under a nitrogen atmosphere. 2-Methylpropylamine (6 ml.) in 10 ml. benzene was added slowly. A gummy solid formed. The mixture was stirred and refluxed using a water separator to collect water formed. After 15 minutes, 5 ml. water was collected. The mixture was refluxed an additional ¾ hour. The solution was concentrated and isopropyl alcohol was added. The crystals which formed were collected and recrystallized from chloroform/isopropyl alcohol to give 4.50 g., m.p. 183°-185° C.

Analysis Calcd. for $C_{15}H_{20}N_2O_3$: C, 65.19; H, 7.30; N, 10.14 Found: C, 64.91; H, 7.34; N, 9.89

EXAMPLE 3

5,6-Dimethoxy-3(4-carbethoxy piperazino)methylene oxindole (VII)

4.0 g. of 5,6-dimethoxy-3-hydroxymethylene oxindole was reacted with N-carbethoxy piperazine as described in Example 2, except that 0.10 g. toluene sulfone acid was added as a catalyst. Yield, 3.05 g. of product, m.p. 172°–174° C.

Analysis Calcd. for $C_{18}H_{28}N_3O_5$: C, 59.82; H, 6.42; N, 11.62 Found: C, 60.01; H, 6.43; N, 11.49

EXAMPLE 4

5,6-Dimethoxy-3(4-furoyl piperazino)methylene oxindole (VIII)

3.0 g. of 5,6-Dimethoxy-3-hydroxymethylene oxindole was reacted with 4.0 g. N-furoyl piperazine as described in Example 2 except that 0.10 g. toluene sulfone acid was added as a catalyst. Yield 3.46 g. of product, m.p. 158°–160° C.

Analysis Calcd. for $C_{20}H_{21}N_3O_5$: C, 62.65; H, 5.52; N, 10.96 Found: C, 62.65; H, 5.61; N, 10.87 [The detailed synthesis of N-furoylpiperazine is more fully described in U.S. Pat. No. 4,026,894.]

EXAMPLE 5

5,6-Dimethoxy-3[4(2-methylpropyloxycarbonyl) piperazino]methylene oxindole (IX)

5.00 g. of 5,6-Dimethoxy-3-hydroxymethylene oxindole, 2.5 g. acetic acid and 6.5 g. piperazine-N-carboxylic acid isobutyl ester (U.S. Pat. No. 3,635,979) in 40 ml. benzene was refluxed using a water separator to remove the water as it formed. After 20 minutes, 200 ml. benzene was added and the solution extracted with potassium carbonate and water. The benzene sollution was treated with magnesium sulfate and charcoal, filtered, concentrated and the residue crystallized from isopropyl alcohol and ether to give 5.50 g. product, m.p. 195°–197° C.

Analysis Calcd. for $C_{20}H_{27}N_3O_5$: C, 61.68; H, 6.99; N, 10.79 Found: C, 61.83; H, 7.02; N, 10.60

EXAMPLE 6

5,6-Dimethoxy-3[4(3,4-dimethoxyphenyl) piperazino]methylene oxindole (X)

3.00 g. of 5,6-Dimethoxy-3-hydroxymethylene oxindole, 2.3 g. acetic acid and 4.1 g. N-(3,4-dimethoxyphenyl)piperazine [J. Med. Chem. 10 (5) 812 (1967)] in 40 ml. benzene were reacted as described in Example 5 to give 4.67 g. product, m.p. 193°–195° C.

Analysis Calcd. for $C_{23}H_{27}N_3O_5$: C, 64.92; H, 6.40; N, 9.88 Found: C, 64.66; H, 6.51; N, 9.64

EXAMPLE 7

Tetrahydropyran-2-carboxylic acid 210 g. of the sodium salt of 3,4-dihydro-2H-pyran-2-carboxylic acid dissolved in 2 liters methanol and hydrogenated at 3 atmosphere pressure over 60 g. haney nickel catalyst. After hydrogen uptake was complete the catalyst was filtered and the solvents removed in vacuo. The residue was acidified with concentrated hydrochloric acid and extracted with chloroform. Distillation gave 143.8 g. product, b.p. 75°–80° C./0.4 mm $N_D^{25} = 1.4633$.

EXAMPLE 8

1-(Tetrahydropyran-2-carbonyl)piperazine

To 20.5 g. tetrahydropyran-2-carboxylic acid in 50 ml. benzene was added 50 g. oxalyl chloride. The solution was gently heated for 2 hours. Vigorous gas evolution resulted. Then, 40 ml. of solvent was distilled through a column at atmospheric pressure. Then, 60 ml. fresh benzene was added and 50 ml. solvent was again distilled at atmospheric pressure. The remainder was dissolved in 150 ml. benzene and added slowly to a solution of 27.4 N-benzyl piperazine and 17.5 g. triethylamine in 200 ml. benzene, while cooling in an ice bath. After addition, the mixture was stirred for 1½ hours at room temperature. Then, 17 g. sodium carbonate in 100 ml. water was added along with 350 ml. benzene. The organic phase was separated after stirring, dried over $MgSO_4$, and concentrated. The residue was dissolved in 200 ml. ethanol and hydrogenated at 3 atmospheres over 10.5 g., 5% paladium catalyst. After uptake of hydrogen ceased, the catalyst was filtered and the product isolated by distillation, b.p. 120°–125° C./0.1 mm solidified to a white solid, m.p. 53°–58° C. Yield: 24.02 g.

EXAMPLE 9

5,6-Dimethoxy-3[4(tetrahydropyran-2-carbonyl) piperazinyl]methylene oxindole (XI)

5.00 g. of 5,6-dimethoxy-3-hydroxymethylene oxindole, 5,6 g. 1-(tetrahydropyran-2-carbonyl)piperazine and 2.1 g. acetic acid in 60 ml. benzene was reacted as described in Example 5 to give 6.18 g. of product, m.p. 208°–210° C.

Analysis Calcd. for $C_{21}H_{27}N_3O_5$: C, 62.82; H, 6.78; N, 10.47 Found: C, 62.88; H, 7.19; N, 10.41

EXAMPLE 10

5,6-Dimethoxy-3[2(3,4-dimethoxyphenyl)ethylamino methylene]oxindole (XII)

5.00 g. of 5,6-Dimethoxy-3-hydroxymethylene oxindole, 6.00 g. of 2(3,4-dimethoxyphenyl)ethylamine and 2.20 acetic acid in 40 ml. benzene was reacted as described in Example 5 to give 6.30 g. product, m.p. 164°–166° C.

Analysis Calcd. for $C_{21}H_{24}N_2O_5$: C, 65.61; H, 6.29; N, 7.29 Found: C, 65.64; H, 6.46; N, 7.18

EXAMPLE 11

5,6-Dimethoxy-3(1-piperidino methylene oxindole (XIII)

4.00 g. of 5,6-Dimethoxy-3-hydroxymethylene oxindole, 3.70 g. piperidine and 25 mg. toluene solfonic acid in 40 ml. benzene were reacted as described in Example 5 to give 1.36 g. of product, m.p. 219°–221° C.

Analysis Calcd. for $C_{16}H_{20}N_2O_3$: C, 66.64; H, 6.99; N, 9.72 Found: C, 66.89; H, 7.07; N, 9.70

EXAMPLE 12

5,6-Dimethoxy-3(4-methyl-1-piperazinomethylene) oxindole (XIV)

5.75 g. of 5,6-Dimethyl-3-hydroxymethylene oxindole, 6.00 g. of N-methyl piperazine and 100 mg. of toluene sulfonic acid in 50 ml. benzene were reacted as described in Example 5, to give 3.00 g. product, m.p. 154°–156° C.

Analysis Calcd. for $C_{16}H_{21}N_3O_3$: C, 63.35; H, 6.98, N, 13.85 Found: C, 62.87; H, 7.15; N, 13.53

EXAMPLE 13

5,6-Dimethoxy-3(3,4-Dimethoxybenzyl)amino methylene oxindole (XV)

5.00 g. of 5,6-Dimethoxy-3-hydroxymethylene oxindole, 6.00 g. of 3,4-dimethoxy benzylamine and 2.20 g. of acetic acid in 40 ml. benzene were reacted as described in Example 5 to give 5.44 g. of product, m.p. 198°-200° C.

Analysis Calcd. for $C_{20}H_{22}N_2O_5$: C, 64.85; H, 5.79; N, 7.56 Found: C, 64.90; H, 6.07; N, 7.51

EXAMPLE 14

5,6-Dimethoxy-3[2-(2-pyridyl)ethyl]methylamino oxindole (XVI)

4.00 g. of 5,6-Dimethoxy-3-hydroxymethylene oxindole, 3.20 g. of 2(2-methylamino ethyl)pyridine and 3.0 g. acetic acid in 50 ml. benzene were reacted as described in Example 5 to give 3.83 g. of product, m.p. 164°-166° C.

Analysis Calcd. for $C_{19}H_{21}N_3O_3$: C, 67.24; H, 6.24; N, 12.38 Found: C, 67.12; H, 6.39; N, 12.29

EXAMPLE 15

Antihypertensive Tests

Tests were carried out with various of the described compounds to determine their antihypertensive effect.

In the tests, the antihypertensive effect of the various compounds were screened in spontaneously hypertensive (SH) rats and found to be potent antihypertensive agents. The screening was conducted as follows:

Male spontaneously hypertensive (SH) rats were trained to be restrained in a wire mesh cylinder in a warming box, at least two training cycles being conducted before testing. The rats were warmed for about ½ hour period to blood pressure measurement, the warming box being maintained at a constant temperature of 35° C.

An occluding cuff attached to the programmed sphymomanometer was placed near the base of the tail of each rat and the pressure in the cuff was increased automatically from 0 to 250 millimeters of mercury (mm Hg) at a rate of 10 mm Hg per second. The total time for each cycle of inflation and deflation of the cuff was 50 seconds and the interval between cycles was one minute.

A photocell was placed distal to the cuff to record the pulses due to forward motion of blood flow with each heart beat. As the pressure in the cuff increased, the pulse disappeared completely at a point where the cuff pressure equaled or exceeded the arterial blood pressure and it reappeared during deflation at approximately the same pressure. Five interference free signals for deflation were recorded for each rat. Rats with a blood pressure of 180 mm Hg or more during the control period were used in the study. Blood pressure and heart rate readings were recorded on a model VII Grass polygraph at intervals of 1, 3, 5 and 24 hours after administration of the drug.

The data obtained from the study is summarized in the following table from which it is apparent that the compounds tested are effective antihypertensive agents which lower the blood pressure of spontaneously hypertensive rats without causing any significant changes in heart rate.

In Table I, the results are of tests on two (2) rats. The compounds were administered intraperitoneally (i.p.) at dosages of 30 mg./kg.

TABLE I

ANTIHYPERTENSIVE EFFECT OF COMPOUNDS IN SPONTANEOUSLY HYPERTENSIVE RATS AT AN INTRAPERITONEAL DOSE OF 30 MG./KG.

| Compound | Percent Change in Blood Pressure (BP) in Two (2) Rats At: | | | |
|---|---|---|---|---|
|  | 1 Hour | 3 Hours | 5 Hours | 24 Hours |
| VI | −14, −13 | −30, −3 | −26, −17 | −14, −10 |
| VII | −36, −33 | −36, −38 | −18, −17 | −2, +2 |
| VIII | −38, −16 | −25, −39 | −10, −12 | −1, −4 |
| IX | −14, −20 | −26, −36 | −23, −18 | −7, +5 |
| X | −31, −45 | −15, −33 | −26, −25 | −27, −28 |
| XI | −22, −15 | −11, −12 | −6, −10 | −18, −14 |
| XII | −11, −1 | −11, −21 | +5, 7 | −1, +2 |
| XIII | 0, −12 | −6, −4 | +2, +5 | −1, +12 |
| XIV | −5, −6 | −4, −2 | −14, −1 | −2, −1 |
| XV | 0, +2 | 0, −6 | −1, −10 | −11, −14 |
| XVI | −14, −18 | −5, −8 | +8, −3 | +8, 0 |

In Table II, the results are of tests on four (4) rats. The compounds were administered orally at dosages of 30 mg./kg. and 100 mg./kg.

TABLE II

ANTIHYPERTENSIVE EFFECT OF COMPOUNDS IN SPONTANEOUSLY HYPERTENSIVE RATS ADMINISTERED ORALLY

| Compound | Dose | Percent Change in Blood Pressure (BP) in Four (4) Rats At: | | | |
|---|---|---|---|---|---|
|  |  | 1 Hour | 3 Hours | 5 Hours | 24 Hours |
| VIII | 30 mg/kg | −12,−15 −11,−25 | −5,+3, −3,−9 | 0,−2, −5,−12 | +6,+1, −4,−5 |
| VII COMPOUNDS 3, | 30 mg/kg | +4 0, | −2,−3, | +4,+1, | + |
| IX | 30 mg/kg | −9,−4 −22,−18, −21,−22 | −10,0 −21,−23, −5,−20 | −10,−18 −21,−21, −17,−18 | −2,−1 −23,−11, −3,−16 |
|  |  | 1 Hour | 4 Hours |  | 24 Hours |
| X | 100 mg/kg | −7,−15, −16 −20 | −33,−38, −35,−37 |  | −6,−11, −9,−10 |

The compounds of this invention can be formulated into various pharmaceutically acceptable dosage forms such as tablets, capsules, pills, and the like, for immediate or sustained release by combining the active compound with suitable pharmaceutically acceptable carriers or diluents according to methods well known in the art. Such dosage forms may include excipients, binders, fillers, flavoring and sweetening agents, and other therapeutically inert ingredients necessary in the formulation of the desired preparation. Preparations for parenteral administration generally include sterile aqueous or nonaqueous solutions, suspensions or emulsions.

We claim:

1. A compound represented by the formula

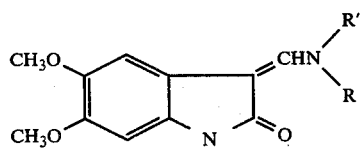

wherein R and R' taken together form a chain of the formula
—$CH_2CH_2NR''CH_2CH_2$— wherein R″ is alkoxycarbonyl.

2. A compound according to claim 1, wherein R″ is

3. A compound according to claim 1, wherein R″ is

4. A pharmaceutical composition comprising an active amount of a compound represented by the formula

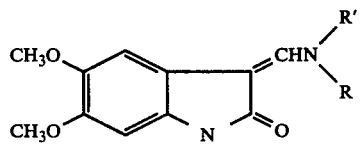

wherein R and R′ taken together form a chain of the formula

wherein R″ is alkoxycarbonyl, or a pharmaceutically acceptable acid addition salt thereof, and a pharmaceutically acceptable carrier.

5. The pharmaceutical composition of claim 4, wherein R″ is

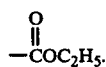

6. The pharmaceutical composition of claim 4, wherein R″ is

7. A method of treating hypertension in a mammal comprising administering to a mammal so afflicted a therapeutically effective amount of a compound represented by the formula

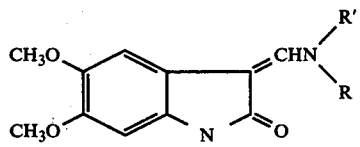

wherein R and R′ taken together form a chain of the formula

wherein R″ is alkoxycarbonyl and the pharmaceutically acceptable acid addition salts thereof.

8. The method of claim 7 wherein R″ is

9. The method of claim 7 wherein R″ is

10. The method of claim 7, wherein the compound is administered interperitoneally to said mammal at a dose ranging from 0.1 to 500 mg./kg. of body weight.

* * * * *